US012606510B2

(12) United States Patent
Sumpena et al.

(10) Patent No.: US 12,606,510 B2
(45) Date of Patent: Apr. 21, 2026

(54) PHENOL RECOVERY OF BISPHENOL-A MOTHER LIQUOR PURGE USING PURIFICATION TRAIN IN THE PHENOL PRODUCTION UNIT

(71) Applicant: SABIC Global Technologies B.V., Bergen op Zoom (NL)

(72) Inventors: Kadek Sumpena, Nederweert (NL); Lara Galan-Sanchez, Eindhoven (NL); Frank Mostert, Maastricht (NL); Kae Shin Wong, Maasmechelen (BE); Martino Trabuio, Eindhoven (NL); Mark Erik Nelson, Mt. Vernon, IN (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 572 days.

(21) Appl. No.: 18/030,638

(22) PCT Filed: Oct. 11, 2021

(86) PCT No.: PCT/IB2021/059293
§ 371 (c)(1),
(2) Date: Apr. 6, 2023

(87) PCT Pub. No.: WO2022/074635
PCT Pub. Date: Apr. 14, 2022

(65) Prior Publication Data
US 2023/0406797 A1      Dec. 21, 2023

Related U.S. Application Data

(60) Provisional application No. 63/090,127, filed on Oct. 9, 2020.

(51) Int. Cl.
*C07C 37/74* (2006.01)
*C07C 1/24* (2006.01)
*C07C 37/52* (2006.01)
*C07C 37/56* (2006.01)

(52) U.S. Cl.
CPC .............. *C07C 37/74* (2013.01); *C07C 1/24* (2013.01); *C07C 37/52* (2013.01); *C07C 37/56* (2013.01)

(58) Field of Classification Search
CPC ......... C07C 37/74; C07C 37/52; C07C 37/56; C07C 1/24
See application file for complete search history.

(56) References Cited

U.S. PATENT DOCUMENTS

| 5,504,251 | A | 4/1996 | Dyckman et al. |
| 6,828,465 | B2 | 12/2004 | Neumann et al. |
| 9,255,053 | B2 * | 2/2016 | Palmer .................. C07C 37/20 |
| 10,246,391 | B2 * | 4/2019 | Nelson .................. C07C 37/005 |
| 2012/0310014 | A1 | 12/2012 | Palmer et al. |
| 2018/0258020 | A1 | 9/2018 | Nelson et al. |

FOREIGN PATENT DOCUMENTS

| JP | H08310978 A | 11/1996 |
| WO | 0172677 A1 | 10/2001 |
| WO | 2008140948 A1 | 11/2008 |
| WO | 2017044229 A1 | 3/2017 |

OTHER PUBLICATIONS

Chinese Second Office Action issued Jun. 5, 2025 for corresponding Chinese Application No. 202180069145.5, English translation, 17 pages.
International Search Report for International Application No. PCT/IB2021/059293; International Filing Date Oct. 11, 2021; Date of Mailing Jan. 18, 2022; 3 pages.
Written Opinion for International Application No. PCT/IB2021/059293; International Filing Date Oct. 11, 2021; Date of Mailing Jan. 18, 2022; 5 pages.
UAE Office Action, issued Apr. 30, 2025, in UAE Application No. P6000818/2023, filed on Apr. 7, 2023, 5 pages.
Chinese First Office Action issued Nov. 29, 2024 for corresponding Chinese Application No. 202180069145.5, English translation, 8 pages.

* cited by examiner

*Primary Examiner* — Sikarl A Witherspoon
(74) *Attorney, Agent, or Firm* — CANTOR COLBURN LLP

(57)      ABSTRACT

Systems and methods for recovering phenol have been disclosed. The methods of recovering phenol includes concurrently processing, in a phenol recovery unit, a crude phenol stream from a phenol production unit, and a bisphenol-A purge stream from a bisphenol-A production unit to produce a first product stream comprising 60 to 95 wt. % phenol. The phenol recovery unit comprises a crude phenol distillation column and a bisphenol-A-phenol distillation column. The processing includes distilling a bottom stream from the crude phenol distillation column in the bisphenol-A-phenol distillation column.

19 Claims, 4 Drawing Sheets

400

COMBINE A CRUDE PHENOL STREAM AND A BISPHENOL-A PURGE STREAM TO FORM A FIRST COMBINED STREAM AS A FEED STREAM TO A CRUDE PHENOL DISTILLATION COLUMN ~ 401

DISTILL THE FIRST COMBINED STREAM IN THE CRUDE PHENOL DISTILLATION COLUMN TO FORM A FIRST TOP STREAM COMPRISING PRIMARILY PHENOL AND A FIRST BOTTOM STREAM COMPRISING PHENOL, PHENOL TAR, AND BISPHENOL-A TAR ~ 402

DISTILL THE FIRST BOTTOM STREAM IN A BISPHENOL-A-PHENOL DISTILLATION COLUMN TO PRODUCE A BISPHENOL-A COLUMN BOTTOM STREAM COMPRISING PRIMARILY PHENOL TAR AND BISPHENOL-A TAR AND AN INTERMEDIATE PHENOL STREAM COMPRISING PHENOL ~ 403

SUBJECT, IN A CRACKING UNIT, BISPHENOL-A COLUMN BOTTOM STREAM TO REACTION CONDITIONS SUFFICIENT TO CRACK THE PHENOL TAR AND/OR THE BISPHENOL-A TAR TO PRODUCE ADDITIONAL PHENOL ~ 404

FLOW THE INTERMEDIATE PHENOL STREAM TO THE CRUDE PHENOL DISTILLATION COLUMN ~ 405

TREAT THE FIRST TOP STREAM IN A HYDROEXTRACTION UNIT TO FORM A FIRST PRODUCT STREAM COMPRISING PRIMARILY PHENOL AND A RECYCLE STREAM ~ 406

DISTILL A CRUDE PHENOL STREAM IN A CRUDE PHENOL DISTILLATION COLUMN TO FORM A SECOND TOP STREAM COMPRISING PRIMARILY PHENOL AND A SECOND BOTTOM STREAM COMPRISING PHENOL, PHENOL TAR, OR COMBINATIONS THEREOF 501 ~

DISTILL A BISPHENOL-A PURGE STREAM AND THE SECOND BOTTOM STREAM IN A BISPHENOL-A-PHENOL DISTILLATION COLUMN TO FORM A SECOND BISPHENOL-A COLUMN BOTTOM STREAM COMPRISING PHENOL TAR AND/OR BISPHENOL-A TAR AND A SECOND INTERMEDIATE PHENOL STREAM COMPRISING PHENOL 502 ~

SUBJECT, IN A CRACKING UNIT, THE SECOND BISPHENOL-A COLUMN BOTTOM STREAM TO REACTION CONDITIONS SUFFICIENT TO CRACK THE PHENOL TAR AND/OR THE BISPHENOL TAR TO PRODUCE ADDITIONAL PHENOL 503 ~

COMBINE THE SECOND INTERMEDIATE PHENOL STREAM WITH THE CRUDE PHENOL STREAM TO FORM SECOND COMBINED STREAM FLOWED INTO THE CRUDE PHENOL DISTILLATION COLUMN 504 ~

TREAT THE SECOND TOP STREAM IN A HYDRO-EXTRACTION UNIT TO FORM A SECOND PRODUCT STREAM COMPRISING PRIMARILY PHENOL AND A SECOND RECYCLE STREAM 505 ~

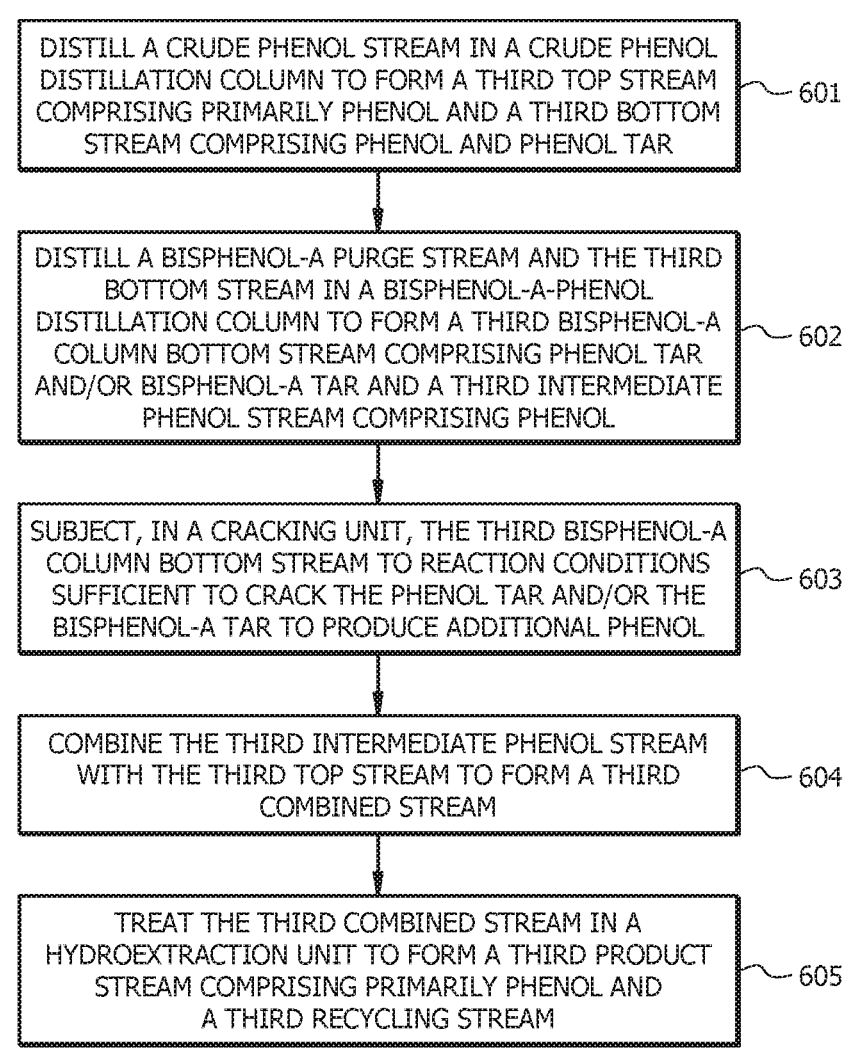

DISTILL A CRUDE PHENOL STREAM IN A CRUDE PHENOL DISTILLATION COLUMN TO FORM A THIRD TOP STREAM COMPRISING PRIMARILY PHENOL AND A THIRD BOTTOM STREAM COMPRISING PHENOL AND PHENOL TAR — 601

DISTILL A BISPHENOL-A PURGE STREAM AND THE THIRD BOTTOM STREAM IN A BISPHENOL-A-PHENOL DISTILLATION COLUMN TO FORM A THIRD BISPHENOL-A COLUMN BOTTOM STREAM COMPRISING PHENOL TAR AND/OR BISPHENOL-A TAR AND A THIRD INTERMEDIATE PHENOL STREAM COMPRISING PHENOL — 602

SUBJECT, IN A CRACKING UNIT, THE THIRD BISPHENOL-A COLUMN BOTTOM STREAM TO REACTION CONDITIONS SUFFICIENT TO CRACK THE PHENOL TAR AND/OR THE BISPHENOL-A TAR TO PRODUCE ADDITIONAL PHENOL — 603

COMBINE THE THIRD INTERMEDIATE PHENOL STREAM WITH THE THIRD TOP STREAM TO FORM A THIRD COMBINED STREAM — 604

TREAT THE THIRD COMBINED STREAM IN A HYDROEXTRACTION UNIT TO FORM A THIRD PRODUCT STREAM COMPRISING PRIMARILY PHENOL AND A THIRD RECYCLING STREAM — 605

*FIG. 2C*

PHENOL RECOVERY OF BISPHENOL-A MOTHER LIQUOR PURGE USING PURIFICATION TRAIN IN THE PHENOL PRODUCTION UNIT

CROSS REFERENCE TO RELATED APPLICATIONS

This application is a National Stage application of PCT/IB2021/059293, filed Oct. 11, 2021, which claims the benefit of priority to U.S. Provisional Patent Application No. 63/090,127, filed Oct. 9, 2020, the entire contents of both are hereby incorporated by reference in their entireties.

FIELD OF INVENTION

The present invention generally relates to phenol recovering processes. More specifically, the present invention relates to a system and a method for recovering phenol from a purge stream of a BPA production unit in a phenol production unit.

BACKGROUND OF THE INVENTION

Phenol is an aromatic compound used as a precursor for many chemicals and materials. It is used for producing plastics including polycarbonates, epoxies, bakelite, and nylon. Phenol is also used in herbicides, and drug production. Bisphenol-A (BPA) is a precursor for various plastic materials, including polycarbonates, polysulfones, and epoxy resins. These plastic materials are used to manufacture water bottles, food containers, sports equipment, water pipes, etc. Thus, there is a large demand for BPA.

Conventionally, phenol along with acetone, is produced by oxidation of cumene followed by a cleavage reaction. BPA is generally produced by a condensation reaction between acetone and phenol in a condensation reactor. The resulting effluent from the condensation reactor is then dehydrated, crystallized and prilled to produce purified BPA prills.

In the conventional process for producing BPA, a BPA production plant sends the dry mother liquor (DML) purge to a cracking unit for phenol recovery. In the conventional phenol production process, a cracking unit comprising multiple columns is used to crack phenol tar to recover phenol. Generally, the phenol recovery step for both BPA and phenol production units consumes a large amount of energy, resulting in high production costs for BPA and/or phenol.

Overall, while the systems and methods for recovering phenol from BPA and phenol production systems exist, the need for improvements in this field persists in light of at least the aforementioned drawbacks of the conventional system and method.

BRIEF SUMMARY OF THE INVENTION

A solution to at least some of the above-mentioned problems associated with systems and methods for recovering phenol from a purge stream flowing from a BPA production system and/or from a crude phenol stream flowing from a phenol production system has been discovered. The solution resides in a method of recovering phenol including concurrently processing a bisphenol-A purge stream (e.g., the mother liquor purge stream) in a phenol recovery system including processing phenol tar from a phenol production unit and bisphenol-A tar from a bisphenol production unit in the same cracker. This can be beneficial for at least reducing the capital expenditure and operation costs compared to conventional methods, which utilize separate crackers for phenol tar and bisphenol-A. Additionally, the disclosed method integrates the phenol production system and bisphenol production system for optimal phenol production, thereby reducing overall phenol consumption for producing bisphenol-A. Therefore, the disclosed method and system of the present invention provide a technical achievement over the conventional systems and methods for recovering phenol from a phenol production process and a bisphenol-A production process.

Embodiments of the invention include a method of recovering phenol. The method comprises concurrently processing, in a phenol recovery system, (i) a crude phenol stream comprising phenol and phenol tar and (ii) a bisphenol-A purge stream comprising phenol and bisphenol-A tar to produce a first product stream comprising 60 to 95 wt. % phenol. The phenol recovery system comprises a crude phenol distillation column and a bisphenol-A-phenol distillation column. The processing comprises distilling a bottom stream from the crude phenol distillation column in the bisphenol-A-phenol distillation column.

Embodiments of the invention include a method of recovering phenol. The method comprises concurrently processing, in a phenol recovery system, (i) a crude phenol stream comprising phenol and phenol tar and (ii) a bisphenol-A purge stream comprising phenol and bisphenol-A tar to produce a first product stream comprising 60 to 95 wt. % phenol. The phenol recovery unit comprises a crude phenol distillation column and a bisphenol-A-phenol distillation column. The processing comprises distilling a bottom stream from the crude phenol distillation column in the bisphenol-A-phenol distillation column. The distilling produces a bisphenol-A-phenol distillation column bottom stream comprising primarily phenol tar and bisphenol-A tar, collectively. The method further comprises subjecting the bisphenol-A-phenol distillation column bottom stream to reaction conditions sufficient to crack the phenol tar and/or the bisphenol-A tar to produce additional phenol.

Embodiments of the invention include a method of recovering phenol. The method comprises concurrently processing, in a phenol recovery unit, (i) a crude phenol stream comprising phenol and phenol tar and (ii) a bisphenol-A purge stream comprising phenol and bisphenol-A tar to produce a first product stream comprising 60 to 95 wt. % phenol. The processing comprises combining the crude phenol stream and the bisphenol-A purge stream to form a feed stream. The processing further comprises distilling the feed stream in the crude phenol distillation column to form a first top stream comprising 85 to 99 wt. % phenol and a first bottom stream comprising phenol and combined phenol tar and bisphenol-A tar. The processing further comprises distilling the first bottom stream in the bisphenol-A-phenol distillation column to produce an intermediate phenol stream comprising phenol and bisphenol-A column bottom stream comprising combined phenol tar and bisphenol-A tar. The processing further comprises distilling the intermediate phenol stream in the crude phenol distillation column to produce additional phenol in the first top stream. The method further comprises subjecting the bisphenol-A column bottom stream to reaction conditions sufficient to crack the phenol tar and/or the bisphenol-A tar to produce additional phenol.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which:

FIGS. 2A-2C show schematic flowcharts for methods of recovering phenol, according to embodiments of the invention.

DETAILED DESCRIPTION OF THE INVENTION

Currently, phenol is recovered by cracking bisphenol-A tar of a bisphenol-A purge stream from a bisphenol-A production unit and/or cracking a phenol tar produced in a phenol production unit in two separate cracking units, resulting in high energy consumption and high production cost for phenol. Additionally, the conventional phenol production unit and bisphenol-A production unit are separate with some of the operation units configured to perform similar processes, resulting in high expenditure and operation costs. The present invention provides a solution to at least some of these problems. The solution is premised on a system and a method for recovering phenol from a bisphenol-A purge stream comprising bisphenol-A tar and a phenol process stream comprising phenol tar in the same cracker, thereby reducing capital expenditure and operating costs. These and other non-limiting aspects of the present invention are discussed in further detail in the following sections.

A. System for Recovering Phenol

Figures 1A, 1B, 1C:
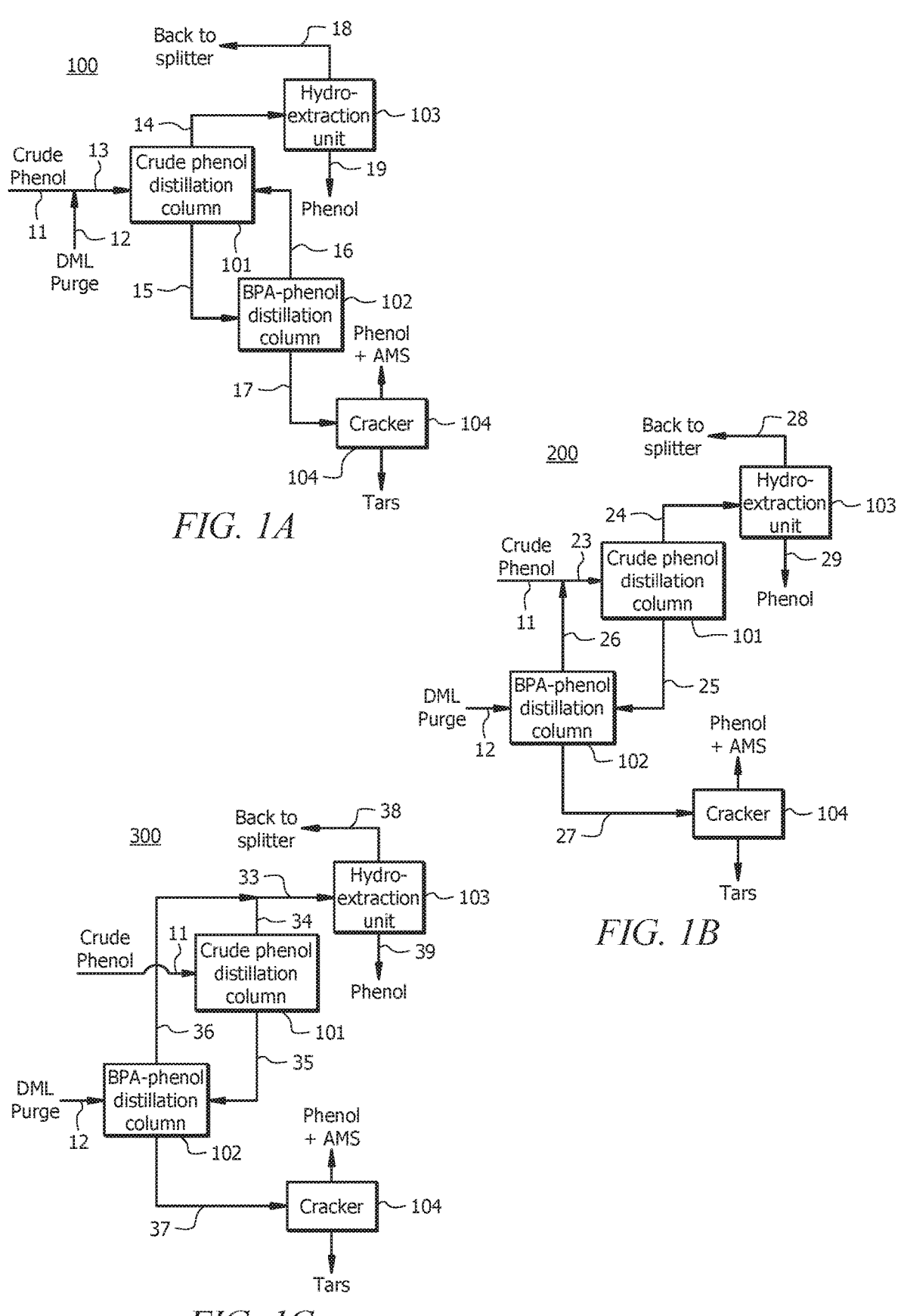
FIGS. 1A-1C show schematic diagrams for systems for recovering phenol, according to embodiments of the invention.

In embodiments of the invention, the system for recovering phenol comprises a crude phenol distillation column, a bisphenol-A-phenol distillation column, a hydro-extraction unit, and a cracker. Notably, the system is capable of processing combined phenol tar and bisphenol-A tar in a single cracker, resulting in reduced capital expenditure and operating costs for recovering phenol and BPA, compared to conventional systems. With reference to FIGS. 1A-1C, schematic diagrams are shown for systems 100, 200, and 300, respectively, which can be used for recovering phenol.

According to embodiments of the invention, as shown in FIG. 1A, 1B, or 1C, system 100, 200, and/or 300 comprise crude phenol distillation column 101. Crude phenol distillation column 101 can be a crude phenol distillation column of a phenol production system. In embodiments of the invention, the phenol production system can include a cumene-based phenol production system comprising an oxidation reaction unit configured to react cumene with air to produce cumene hydroperoxide (CHP), a cumene stripping unit configured to strip cumene from the effluent of the oxidation reaction unit, a cleavage unit configured to decompose the cumene hydroperoxide to produce phenol and acetone under acidic reaction conditions, a neutralization unit configured to neutralize an effluent of the cleavage unit to produce a first wastewater stream and a neutralized phenol stream. The phenol production system further comprises an acetone fraction unit configured to separate the neutralized phenol stream to produce crude phenol stream 11 comprising primarily phenol. Crude phenol stream 11 can further comprise cumene, alpha-methylstyrene (AMS), heavy components, or combinations thereof.

According to embodiments of the invention, an outlet of crude phenol distillation column 101 is in fluid communication with an inlet of bisphenol-A-phenol distillation column 102. In embodiments of the invention, bisphenol-A-phenol distillation column 102 may include a bisphenol-A-phenol distillation column of a BPA production system.

In embodiments of the invention, the BPA production system includes a bisphenol-A synthesis reactor configured to react acetone with phenol to produce BPA, a dehydration unit configured to remove water from an effluent from the condensation reaction unit comprising one or more BPA synthesis reactors to produce a second wastewater stream comprising phenol and water, and a crude BPA stream comprising BPA. The crude BPA stream may include 5 to 25 wt. % BPA. In embodiments of the invention, the second wastewater stream further comprises acetone and/or sodium hydroxide. The BPA production system may further comprise a BPA concentration unit configured to concentrate the crude BPA stream, and an adduct crystallization unit configured to crystalize BPA of an effluent from the concentration unit to produce (1) crystalized BPA and (2) a mother liquor comprising bisphenol-A tar, a solvent, and water. The BPA production system may further comprise a solvent recovery unit configured to recover the solvent from the mother liquor and produce a dry mother liquor (DML) stream. The dry mother liquor stream is further split to form a dry mother liquor (DML) purge stream comprising the bisphenol-A tar, a solvent, and water. In embodiments of the invention, the BPA production system is located near the phenol production system.

According to embodiments of the invention, in system 100 as shown in FIG. 1A, crude phenol stream 11 and bisphenol-A purge stream 12 can form first combined stream 13. Bisphenol-A purge stream 12 may include the mother liquor purge stream from the BPA production system. In embodiments of the invention, crude phenol distillation column 101 is configured to distill first combined stream 13 to produce first top stream 14 comprising primarily phenol and first bottom stream 15 comprising phenol, combined phenol tar and bisphenol-A tar. Phenol tar can include acetophenone, dimethylbenzylalcohol, o,p-cumylphenol, alphamethylstyrene dimer, phenol, or combinations thereof. Bisphenol-A tar can include p,p-bisphenol-A, o,p-bisphenol-A, isopropenyl phenol, Chroman, BPX, isopropenyl phenol dimers, spirobi, or combinations thereof.

According to embodiments of the invention, an outlet of crude phenol distillation column 101 is in fluid communication with an inlet of bisphenol-A-phenol distillation column 102 such that first bottom stream 15 flows from crude phenol distillation column 101 to bisphenol-A-phenol distillation column 102. Bisphenol-A-phenol distillation column 102 may be configured to distill first bottom stream 15 to produce intermediate phenol stream 16 comprising phenol and bisphenol-A column bottom stream 17 comprising phenol tar and bisphenol-A tar. Intermediate phenol stream 16 may further include alpha-methyl styrene, hydroxyl acetone, and 2-methyl benzyl furan. An outlet of bisphenol-A-phenol distillation column 102 may be in fluid communication with an inlet of crude phenol distillation column 101 such that intermediate phenol stream 16 flows from bisphenol-A-phenol distillation column 102 to crude phenol distillation column 101.

According to embodiments of the invention, an outlet of crude phenol distillation column 101 is in fluid communication with hydro-extraction unit 103 such that first top stream 14 flows from crude distillation column 101 to hydro-extraction unit 103. Hydro-extraction unit 103 may be configured to separate first top stream 14 to produce first product stream 19 comprising primarily phenol and recycle stream 18. Recycle stream 18 may comprise 0.5 to 2 wt. % phenol. Recycle stream 18 may be recycled to phenol-acetone separation unit, where light components, such as acetone, exist from the top of a distillation column are further purified in an acetone purification train. In embodiments of the invention, as shown in FIG. 1A, an outlet of bisphenol-A-phenol distillation column 102 is in fluid communication with cracking unit 104 such that bisphenol-A column bottom stream 17 flows from bisphenol-A-phenol distillation column 102 to cracking unit 104. Cracking unit 104 can be configured to crack phenol tar and/or bisphenol-A tar in bisphenol-A column bottom stream 17 to produce a tar stream comprising isopropenyl phenol, isopropenyl phenol dimers and a cracker product stream comprising phenol and/or alpha-methylstyrene (AMS).

According to embodiments of the invention, in system 200, as shown in FIG. 1B, crude phenol distillation column 101 is configured to distill crude phenol stream 11 to produce second top stream 24 comprising primarily phenol and second bottom stream 25 comprising phenol tar and phenol. Bisphenol-A-phenol distillation column 102, in system 200 as shown in FIG. 1B is configured to distill bisphenol-A purge stream 12 and second bottom stream 25 to produce second intermediate phenol stream 26 comprising phenol and second bisphenol-A column bottom stream 27 comprising phenol tar and bisphenol-A tar. Second intermediate phenol stream 26 may be combined with crude phenol stream 11 to form second combined stream 23 as feed stream of crude phenol distillation column 101. In embodiments of the invention, as shown in FIG. 1B, second top stream 24 is flowed into hydro-extraction unit 103. Hydro-extraction unit 103 may be configured to separate second top stream 24 via hydro-extraction to produce second product stream 29 comprising primarily phenol and second recycle stream 28. Second recycle stream may comprises 0.5 to 2 wt. % phenol. In embodiments of the invention, as shown in FIG. 1B, second bisphenol-A column bottom stream 27 is flowed to cracking unit 104. Cracking unit 104 may be configured to crack phenol tar and/or bisphenol-A tar of second bisphenol-A column bottom stream 27 to produce a tar stream comprising isopropenyl phenol, isopropenyl phenol dimers, and a cracker product stream comprising phenol and/or alpha-methylstyrene (AMS).

According to embodiments of the invention, in system 300, as shown in FIG. 1C, crude phenol distillation column 101 is configured to distill crude phenol stream 11 to produce third top stream 34 comprising primarily phenol and third bottom stream 35 comprising phenol tar and phenol. Bisphenol-A-phenol distillation column 102, in system 300 as shown in FIG. 1C, can be configured to distill bisphenol-A purge stream 12 and third bottom stream 35 to produce third intermediate phenol stream 36 comprising phenol and third bisphenol-A column bottom stream 37 comprising phenol tar and bisphenol-A tar. Third intermediate phenol stream 36 may be combined with third top stream 34 to form third combined stream 33. In embodiments of the invention, as shown in FIG. 1C, third combined stream 33 is flowed into hydro-extraction unit 103. Hydro-extraction unit 103 may be configured to separate third combined stream 33 to produce third product stream 39 comprising primarily phenol and third recycle stream 38. Third recycle stream 38 may comprise 0.5 to 2 wt. % phenol. In embodiments of the invention, as shown in FIG. 1C, third bisphenol-A column bottom stream 37 is flowed to cracking unit 104. Cracking unit 104 may be configured to crack phenol tar and/or bisphenol-A tar in third bisphenol-A column bottom stream 37 to produce a tar stream comprising isopropenyl phenol, isopropenyl phenol dimers, and a cracker product stream comprising phenol and/or alpha-methylstyrene (AMS).

B. Method of Recovering Phenol

Methods for recovering phenol from a crude phenol stream of a phenol production system and a DML purge stream from a BPA production system have been discovered. As shown in FIGS. 2A-2C, embodiments of the invention include methods 400, 500, and 600 for recovering phenol. Methods 400, 500, 600 may be implemented by systems 100, 200, and 300, respectively, as shown in FIGS. 1A-1C, and described above. Each of methods 400, 500, and 600 can comprise concurrent processing, in system 100, 200, or 300, of (i) crude phenol stream 11 comprising phenol and phenol tar and (ii) bisphenol-A purge stream 12 comprising phenol and bisphenol-A tar to produce a product stream. In embodiments of the invention, the product stream comprises 60 to 95 wt. % phenol and all ranges and values there between including ranges of 60 to 65 wt. %, 65 to 70 wt. %, 70 to 75 wt. %, 75 to 80 wt. %, 80 to 85 wt. %, 85 to 90 wt. %, and 90 to 95 wt. %. Bisphenol-A purge stream 12 can include a mother liquor purge stream from a bisphenol-A production system.

According to embodiments of the invention, as shown in block 401 of method 400, processing of method 400 includes combining crude phenol stream 11 and bisphenol-A purge stream 12 to form first combined stream 13 as a feed stream to crude phenol distillation column 101. Bisphenol-A purge stream 12 may include a dry mother liquor purge stream from a bisphenol-A production system. In embodiments of the invention, at block 401, crude phenol stream 11 and bisphenol-A purge stream 12 may be combined at a volumetric ratio in a range of 1 to 20 and all ranges and values there between including ranges of 1 to 2, 2 to 4, 4 to 6, 6 to 8, 8 to 10, 10 to 12, 12 to 14, 14 to 16, 16 to 18, and 18 to 20.

According to embodiments of the invention, as shown in block 402, processing of method 400 includes distilling first combined stream 13 in crude phenol distillation column 101 to form first top stream 14 comprising primarily phenol and first bottom stream 15 comprising phenol, phenol tar, and bisphenol-A tar. In embodiments of the invention, first top stream 14 comprises 85 to 99 wt. % phenol. First bottom stream 15 may comprise 2 to 15 wt. % phenol, and 85 to 98 wt. % combined phenol tar and bisphenol-A tar. In embodiments of the invention, at block 402, crude phenol distillation column 101 is operated at an overhead temperature range of 120 to 150° C. and a bottom temperature range of 180 to 220° C. Crude phenol distillation column 101 may be operated at an operating pressure in a range of 0.1 to bar and all ranges and values there between including ranges of 0.1 to 0.2 bar, 0.2 to 0.3 bar, 0.3 to 0.4 bar, and 0.4 to 0.5 bar. Crude phenol distillation column 101 may be operated at a temperature in a range of 50 to 250° C. and all ranges and values there between including ranges of 50 to 70° C., 70 to 90° C., 90 to 110° C., 110 to 130° C., 130 to 150° C., 150 to 170° C., and 170 to 190° C.

According to embodiments of the invention, as shown in block 403, processing of method 400 includes distilling first bottom stream 15 in bisphenol-A-phenol distillation column 102 to produce bisphenol-A column bottom stream 17 comprising primarily phenol tar and bisphenol-A tar and intermediate phenol stream 16 comprising phenol. In embodiments of the invention, at block 403, bisphenol-A-phenol distillation column 102 is operated at an overhead temperature of 80 to 120° C., a bottom temperature of 150 to 200° C., and an operating pressure of 0.2 to 0.8 bar. Bisphenol-A column bottom stream 17 may comprise 5 to 20 wt. % combined phenol tar and bisphenol-A tar. Intermediate phenol stream 16 may comprise 60 to 98 wt. % phenol.

According to embodiments of the invention, as shown in block 404, processing of method 400 includes subjecting, in cracking unit 104, bisphenol-A column bottom stream 17 to reaction conditions sufficient to crack the phenol tar and/or the bisphenol-A tar to produce additional phenol. The step of subjecting at block 404 may further produce tars, and/or AMS. In embodiments of the invention, the subjecting at block 404 may include contacting bisphenol-A column bottom stream 17 with an acidic catalyst comprising sulfonic acid, hydrochloric acid, nitric acid, or combinations thereof. In embodiments of the invention, at block 404, cracking unit 104 is operated at an operating temperature of 100 to 250° C. and a pressure of 0.2 to 1.5 bar. According to embodiments of the invention, as shown in block 405, processing of method 400 includes flowing intermediate phenol stream 16 into crude phenol distillation column 101.

According to embodiments of the invention, as shown in block 406, processing of method 400 includes treating first top stream 14 in hydro-extraction unit 103 to form first product stream 19 comprising primarily phenol and recycle stream 18 comprising phenol, alpha-methyl styrene, and acetone. At block 406, hydro-extraction unit 103 can include a hydro-extraction column. The hydro-extraction column may be operated at an extraction temperature of 100 to 250° C. and extraction pressure of 0.4 to 2.0 bar. Hydro-extraction unit 103 at block 406 may be operated using a solvent comprising water, hydroxyl acetone, and 2-methyl benzyl furan. In embodiments of the invention, recycle stream 18 is flowed to a phenol-acetone separation column.

According to embodiments of the invention, as shown in block 501 of method 500, processing of method 500 includes distilling crude phenol stream 11 in crude phenol distillation column 101 to form second top stream 24 comprising primarily phenol, and second bottom stream 25 comprising phenol, phenol tar, and combinations thereof. In embodiments of the invention, second top stream 24 comprises 85 to 99 wt. % phenol. In embodiments of the invention, at block 501, crude phenol distillation column 101 is operated at an overhead temperature range of 40 to 150° C. and a bottom temperature range of 80 to 250° C. Crude phenol distillation column 101 may be operated at an operating pressure in a range of 0.2 to bar and all ranges and values there between including ranges of 0.2 to 0.3 bar, 0.3 to 0.4 bar, 0.4 to 0.5 bar, 0.5 to 0.6 bar, 0.6 to 0.7 bar, and 0.7 to 0.8 bar.

According to embodiments of the invention, as shown in block 502, processing of method 500 includes distilling bisphenol-A purge stream 12 and second bottom stream 25 in bisphenol-A-phenol distillation column 102 to form (1) second bisphenol-A column bottom stream 27 comprising phenol, phenol tar, and bisphenol-A tar, and (2) second intermediate phenol stream 26 comprising phenol. In embodiments of the invention, at block 502, bisphenol-A-phenol distillation column 102 is operated at an overhead temperature of 80 to 120° C., a bottom temperature of 150 to 200° C., and an operating pressure of 0.2 to 0.8 bar. Second Bisphenol-A column bottom stream 27 may comprise 85 to 98 wt. % combined phenol tar and bisphenol-A tar and 2 to 15 wt. % phenol. Second intermediate phenol stream 26 may comprise 60 to 98 wt. % phenol and all ranges and values there between including ranges of 60 to 64 wt. %, 68 to 72 wt. %, 72 to 76 wt. %, 76 to 80 wt. %, 80 to 84 wt. %, 84 to 88 wt. %, 88 to 92 wt. %, 92 to 96 wt. %, and 96 to 98 wt. %.

According to embodiments of the invention, as shown in block 503, processing of method 500 includes subjecting, in cracking unit 104, second bisphenol-A column bottom stream 27 to reaction conditions sufficient to crack the phenol tar and/or the bisphenol tar to produce additional phenol. The step of subjecting at block 503 may further produce tars, and/or AMS. In embodiments of the invention, the subjecting at block 503 may include contacting second bisphenol-A column bottom stream 27 with an acidic catalyst comprising sulfonic acid, hydrochloric acid, nitric acid, or combinations thereof. In embodiments of the invention, at block 503, reaction conditions in cracking unit 104 can include an operating temperature of 80 to 300° C. and an operating pressure of 0.5 to 2 bar. According to embodiments of the invention, as shown in block 504, processing of method 500 may include combining second intermediate phenol stream 26 with crude phenol stream 11 to form second combined stream 23, which is flowed into crude phenol distillation column 101.

According to embodiments of the invention, as shown in block 505, processing of method 500 includes treating second top stream 24 in hydro-extraction unit 103 to form second product stream 29 comprising primarily phenol and second recycle stream 28 comprising phenol, acetone, and alpha methyl styrene. At block 505, hydro-extraction unit 103 can include a hydro-extraction column. The hydro-extraction column may be operated at an extraction temperature of 100 to 250° C. and extraction pressure of 0.4 to 2.0 bar. Hydro-extraction unit 103 at block 505 may be operated using a solvent comprising water, hydroxyl acetone, and 2-methyl benzyl furan. In embodiments of the invention, second recycle stream 28 is flowed to a phenol-acetone separation column. Second product stream 29 may comprise 65% to 95 wt. % phenol and all ranges and values there between including ranges of 65 to 70 wt. %, 70 to 75 wt. %, 75 to 80 wt. %, 80 to 85 wt. %, 85 to 90 wt. %, and 90 to 95 wt. %.

According to embodiments of the invention, as shown in block 601 of method 600, processing of method 600 includes distilling crude phenol stream 11 in crude phenol distillation column 101 to form third top stream 34 comprising primarily phenol, and third bottom stream 35 comprising phenol and phenol tar. In embodiments of the invention, third top stream 34 comprises 85 to 99 wt. % phenol. In embodiments of the invention, at block 601, crude phenol distillation column 101 is operated at an overhead temperature range of 40 to 150° C. and a bottom temperature range of 80 to 250° C. Crude phenol distillation column 101 may be operated at an operating pressure in a range of 0.2 to 0.8 bar and all ranges and values there between including ranges of 0.2 to 0.3 bar, 0.3 to 0.4 bar, 0.4 to 0.5 bar, 0.5 to 0.6 bar, 0.6 to bar, and 0.7 to 0.8 bar.

According to embodiments of the invention, as shown in block 602, processing of method 600 includes distilling bisphenol-A purge stream 12 and third bottom stream 35 in bisphenol-A-phenol distillation column 102 to form third bisphenol-A column bottom stream 37 comprising phenol tar and/or bisphenol-A tar, and third intermediate phenol stream 36 comprising phenol. In embodiments of the invention, at block 602, bisphenol-A-phenol distillation column 102 is operated at an overhead temperature of 80 to 120° C., a bottom temperature of 150 to 200° C., and an operating pressure of 0.2 to 0.8 bar. Third bisphenol-A column bottom stream 37 may comprise 2 to 15 wt. % phenol, and 85 to 98 wt. % combined phenol tar and bisphenol-A tar. Third intermediate phenol stream 36 may comprise 60 to 98 wt. % phenol.

According to embodiments of the invention, as shown in block 603, processing of method 600 includes subjecting, in cracking unit 104, third bisphenol-A column bottom stream 37 to reaction conditions sufficient to crack the phenol tar and/or the bisphenol-A tar to produce additional phenol. The step of subjecting at block 603 may further produce tars, and/or AMS. In embodiments of the invention, the subjecting at block 603 may include contacting third bisphenol-A column bottom stream 37 with an acidic catalyst comprising sulfonic acid, hydrochloric acid, nitric acid, or combinations thereof. In embodiments of the invention, at block 603, cracking unit 104 is operated at an operating temperature of 80 to 300° C. and a pressure of 0.5 to 2 bar. According to embodiments of the invention, as shown in block 604, processing of method 600 may include combining third intermediate phenol stream 36 with third top stream 34 to form third combined stream 33.

According to embodiments of the invention, as shown in block 605, processing of method 600 includes treating third combined stream 33 in hydro-extraction unit 103 to form third product stream 39 comprising primarily phenol and third recycle stream 38 comprising phenol, acetone, and alpha-methyl styrene. Third product stream 39 may include 60 to 95 wt. % phenol. At block 605, hydro-extraction unit 103 can include a hydro-extraction column. The hydro-extraction column may be operated at an extraction temperature of 100 to 250° C. and extraction pressure of 0.4 to 2.0 bar. Hydro-extraction unit 103 at block 605 may be operated using a solvent comprising water, hydroxyl acetone, and 2-methyl benzyl furan. In embodiments of the invention, third recycle stream 38 is flowed to a phenol-acetone separation column.

Although embodiments of the present invention have been described with reference to blocks of FIGS. 2A, 2B, and 2C should be appreciated that operation of the present invention is not limited to the particular blocks and/or the particular order of the blocks illustrated in FIGS. 2A, 2B, and 2C. Accordingly, embodiments of the invention may provide functionality as described herein using various blocks in a sequence different than that of FIGS. 2A, 2B, and 2C.

The systems and processes described herein can also include various equipment that is not shown and is known to one of skill in the art of chemical processing. For example, some controllers, piping, computers, valves, pumps, heaters, thermocouples, pressure indicators, mixers, heat exchangers, and the like may not be shown.

As part of the disclosure of the present invention, specific examples are included below. The examples are for illustrative purposes only and are not intended to limit the invention. Those of ordinary skill in the art will readily recognize parameters that can be changed or modified to yield essentially the same results.

EXAMPLES

Simulations of the systems as shown in FIGS. 1A (system 100) and 1B (system 200) were run in ASPEN HYSIS version 10 platform. The operating parameters for system 100 are shown in Table 1.

TABLE 1

| Operating parameters for System 100 | | | |
| --- | --- | --- | --- |
| | Crude phenol distillation column 101 | BPA-phenol distillation column 102 | Cracker 104 |
| Bottom temperature (° C.) | 138 | 138 | 150 |
| Top temperature (° C.) | 205 | 205 | 150 |
| Top pressure [psig] | −9.475 | −14.12 | −13.14 |
| Bottom pressure | −1.74 | −14.02 | −13.14 |

TABLE 1-continued

| | Crude phenol distillation column 101 | BPA-phenol distillation column 102 | Cracker 104 |
|---|---|---|---|
| Operating parameters for System 100 | | | |
| [psig] | | | |
| Trays | 45 | 9 | — |

TABLE 2 streams composition for System 100

| Streams | 13 | 15 | 17 | Cracker outlet |
|---|---|---|---|---|
| Total flowrate (lb/hr) | 161771 | 84622 | 8864 | 8864 |
| Phenol (wt. %) | 63.5 | 37.5 | 3 | 35.4 |
| Ketone (wt. %) | 24.3 | 48.0 | 4.0 | 5.8 |
| Carbinol (wt. %) | 5.1 | 8.9 | 8.3 | 0 |
| Alpha-methylstyrene (wt. %) | 1.2 | 0 | 0 | 33.3 |
| Cumylphenol (wt. %) | 1.5 | 1.7 | 26.1 | 1.3 |
| Others (wt. %) | 4.4 | 3.9 | 58.6 | 24.2 |

TABLE 3 operating parameters for non-integrated system

| | Crude phenol distillation column 101 | BPA-phenol distillation column 102 | Cracker 104 |
|---|---|---|---|
| Bottom temperature (° C.) | 138 | 138 | 150 |
| Top temperature (° C.) | 205 | 205 | |
| Top pressure [psig] | −9.475 | −14.0 | −13.14 |
| Bottom pressure [psig] | −1.74 | −13.14 | |
| Trays | 45 | 9 | — |

TABLE 4 streams composition for non-integrated system

| Streams | Inlet Crude phenol distillation column 101 | Inlet BPA-phenol distillation column 102 | Inlet Cracker 104 | Outlet Cracker 104 |
|---|---|---|---|---|
| Total flowrate (lb/hr) | 82975 | 15570 | 9635 | 9635 |
| Phenol (wt. %) | 90.0 | 78.2 | 7.5 | 37.2 |
| Ketone (wt. %) | 0 | 0 | 5.7 | 7.4 |
| Carbinol (wt. %) | 1.0 | 0 | 8.3 | 0 |
| Alpha-methylstyrene (wt. %) | 2.2 | 0 | 0 | 31.1 |
| Cumylphenol (wt. %) | 2.8 | 0 | 24 | 1.2 |
| Others (wt. %) | 4 | 21.8 | 54.5 | 24.3 |

Figure 3:
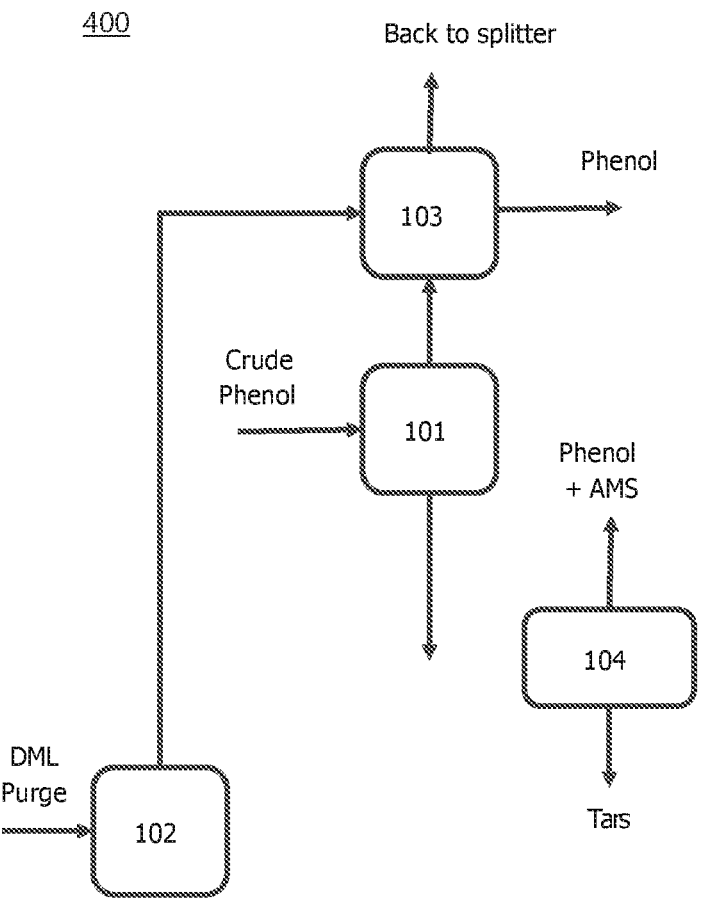
FIG. 3 shows a non-integrated system for recovering phenol.

Tables 1-4 show the comparative examples of integrated configuration (FIG. 1A) and non-integrated configuration 400 (FIG. 3). Under the same operating conditions of columns 101, 102, 103 and 104, configuration 1A (column 101 and 102) is more effective for recovering phenol, leading to lesser phenol at the inlet of the cracker.

In the context of the present invention, at least the following 20 embodiments are described. Embodiment 1 is a method of recovering phenol. The method includes concurrently processing, in a phenol recovery system, (i) a crude phenol stream containing phenol and phenol tar and (ii) a bisphenol-A purge stream containing phenol and bisphenol-A tar to produce a first product stream containing 60 to 95 wt. % phenol, wherein the phenol recovery system includes a crude phenol distillation column and a bisphenol-A-phenol distillation column and the processing includes distilling a bottom stream from the crude phenol distillation column in the bisphenol-A-phenol distillation column. Embodiment 2 is the method of embodiment 1, wherein the bottom stream from the crude phenol distillation column contains 2 to 15 wt. % phenol, and 85 to 98 wt. % combined phenol tar and bisphenol-A tar. Embodiment 3 is the method of embodiment 2, wherein the distilling of the bottom stream produces a bisphenol-A-phenol distillation column bottom stream containing primarily phenol tar and bisphenol-A tar, collectively. Embodiment 4 is the method of embodiment 3, further including subjecting the bisphenol-A column bottom stream to reaction conditions sufficient to crack the phenol tar and/or the bisphenol-A tar to produce additional phenol. Embodiment 5 is the method of embodiment 4, wherein the subjecting step further produces α-methylstyrene. Embodiment 6 is the method of either of embodiments 4 or 5, wherein the reaction conditions for the subjecting step include a reaction temperature of 100 to 250° C. and a reaction pressure of 0.2 to 1.5 bar. Embodiment 7 is the method of any of embodiments 4 to 6, wherein the subjecting step includes contacting the bisphenol column bottom stream with an acidic catalyst selected from the group consisting of sulfonic acid, hydrochloric acid, nitric acid, and combinations thereof. Embodiment 8 is the method of any of embodiments 1 to 7, wherein the phenol tar contains acetophenone, dimethylbenzylalcohol, o,p-cumylphenol, alphamethylstyrene dimer, phenol, or combinations thereof. Embodiment 9 is the method of any of embodiments 1 to 8, wherein the bisphenol-A tar contains p,p-bisphenol-A, o,p-bisphenol-A, isopropenyl phenol, Chroman, BPX, isopropenyl phenol dimers, spirobi, or combinations thereof. Embodiment 10 is the method of any of embodiments 1 to 9, wherein the processing includes combining the crude phenol stream and the bisphenol-A purge stream to form a feed stream. The method further includes distilling the feed stream in the crude phenol distillation column to form a first top stream containing 85 to 99 wt. % phenol and a first bottom stream containing phenol, combined phenol tar and bisphenol-A tar, wherein the first distilling of the bottom stream in the bisphenol-A phenol distillation column further produces an intermediate phenol stream containing phenol. Embodiment 11 is the method of embodiment 10, wherein the processing further includes distilling the intermediate phenol stream in the crude phenol distillation column to produce additional phenol in the first top stream. Embodiment 12 is the method of either of embodiments 10 or 11, wherein the processing further includes treating the first top stream in a hydro-extraction unit to produce the first product stream containing 60 to 95 wt. % phenol and a recycle stream containing 0.5 to 2 wt. % phenol. Embodiment 13 is the method of any of embodiments 1 to 9, wherein the processing includes distilling the crude phenol stream in the crude phenol distillation column to form a second top stream containing 85 to 99 wt. % phenol and a second bottom stream from the crude phenol distillation column containing phenol, phenol tar, and bisphenol-A tar. The method further includes distilling the bisphenol-A purge stream and the bottom stream in the bisphenol-A-phenol distillation column to form a second bisphenol column bottom stream, and a second intermediate phenol stream containing phenol. Embodiment 14 is the method of embodiment 13, wherein the processing further includes combining at least a portion of the second intermediate phenol stream with the crude phenol stream to form a second combined stream. The method further includes distilling the second combined stream in the crude phenol distillation column. Embodiment 15 is the method of either of embodiments 13 or 14, wherein the processing further includes combining at least a portion of the second intermediate phenol stream with the second top stream to form a third combined stream containing primarily phenol. The method also includes processing the third combined stream in a hydro-extraction unit to form the first product stream containing 60 to 95 wt. % phenol and a recycle stream containing 0.5 to 2 wt. % phenol. Embodiment 16 is the method of any of embodiments 13 to 15, wherein the hydro-extraction unit is operated at an extraction temperature of 100 to 250° C. and an extraction pressure of 0.4 to 2 bar. Embodiment 17 is the method of any of embodiments 13 to 16, wherein the crude phenol distillation column is operated at an overhead temperature range of 120 to 150° C., a reboiler range of 180 to 220° C., and an operating pressure of 0.1 to 0.5 bar. Embodiment 18 is the method of any of embodiments 13 to 17, wherein the bisphenol-A-phenol distillation column is operated at an overhead temperature range of 80 to 120° C., a reboiler range of 150 to 200° C., and an operating pressure of 0.1 to 0.7 bar. Embodiment 19 is the method of any of embodiments 1 to 18, wherein the crude phenol stream is produced by separating an effluent of a cumene based phenol production process. Embodiment 20 is the method of any of embodiments 1 to 19, wherein the bisphenol-A purge stream includes a bisphenol-A dry mother liquor purge stream generated by crystallization of bisphenol-A from an effluent of a bisphenol-A synthesis reactor.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of recovering phenol, the method comprising:
   concurrently processing, in a phenol recovery system, (i) a crude phenol stream comprising phenol and phenol tar and (ii) a bisphenol-A purge stream comprising phenol and bisphenol-A tar;
   wherein the phenol recovery system comprises a crude phenol distillation column and a bisphenol-A-phenol distillation column and the processing comprises:

distilling the crude phenol stream in the crude phenol distillation column to form a top stream comprising 85 to 99 wt. % phenol and a bottom stream, and
   distilling the bottom stream in the bisphenol-A-phenol distillation column.

2. The method of claim 1, wherein the bottom stream comprises 2 to 15 wt. % phenol, and 85 to 98 wt. % combined phenol tar and bisphenol-A tar.

3. The method of claim 2, wherein the distilling of the bottom stream produces a bisphenol-A-phenol distillation column bottom stream comprising primarily phenol tar and bisphenol-A tar, collectively.

4. The method of claim 3, further comprising:
   subjecting the bisphenol-A-phenol distillation column bottom stream to reaction conditions sufficient to crack the phenol tar and/or the bisphenol-A tar to produce additional phenol and α-methylstyrene.

5. The method of claim 4, wherein the reaction conditions for the subjecting step comprise a reaction temperature of 100 to 250° C. and a reaction pressure of 0.2 to 1.5 bar.

6. The method of claim 4, wherein the subjecting step comprises:
   contacting the bisphenol-A-phenol distillation column bottom stream with sulfonic acid.

7. The method of claim 1, wherein the phenol tar comprises acetophenone, dimethylbenzylalcohol, o-cumylphenol, p-cumylphenol, alphamethylstyrene dimers, phenol, or combinations thereof.

8. The method of claim 1, wherein the bisphenol-A tar comprises p,p-bisphenol-A, o,p-bisphenol-A, isopropenyl phenol, Chroman, BPX, isopropenyl phenol dimers, spiro-biindane bisphenol, or combinations thereof.

9. The method of claim 1, wherein:
   the processing comprises combining the crude phenol stream and the bisphenol-A purge stream to form a feed stream;
   the bottom stream comprises phenol, combined phenol tar and bisphenol-A tar; and
   distilling of the bottom stream in the bisphenol-A phenol distillation column further produces an intermediate phenol stream comprising phenol.

10. The method of claim 9, wherein the processing further comprises:
    distilling the intermediate phenol stream in the crude phenol distillation column to produce additional phenol in the top stream.

11. The method of claim 9, wherein the processing further comprises:
    treating the top stream in a hydro-extraction unit to produce a first product stream and a recycle stream comprising 0.5 to 2 wt. % phenol.

12. The method of claim 1, wherein:
    the bottom stream comprises phenol, phenol tar, and bisphenol-A tar; and
    the processing comprises distilling the bisphenol-A purge stream and the bottom stream in the bisphenol-A-phenol distillation column to form a bisphenol-A-phenol distillation column bottom stream, and an intermediate phenol stream comprising phenol.

13. The method of claim 12, wherein the processing further comprises:
    combining at least a portion of the intermediate phenol stream with the crude phenol stream to form a combined stream comprising at least the portion of the intermediate phenol stream and the crude phenol stream; and distilling the combined stream comprising at least the portion of the intermediate phenol stream and the crude phenol stream in the crude phenol distillation column.

14. The method of claim 12, wherein the processing further comprises:

combining at least a portion of the second intermediate phenol stream with the top stream to form a combined stream comprising primarily phenol; and processing the combined stream comprising primarily phenol in a hydro-extraction unit to form a first product stream and a recycle stream comprising 0.5 to 2 wt. % phenol.

15. The method of claim 12, wherein the hydro-extraction unit is operated at an extraction temperature of 100 to 250° C. and an extraction pressure of 0.4 to 2 bar.

16. The method of claim 12, wherein the crude phenol distillation column is operated at an overhead temperature range of 120 to 150° C., a reboiler range of 180 to 220° C., and an operating pressure of 0.1 to 0.5 bar.

17. The method of claim 12, wherein the bisphenol-A-phenol distillation column is operated at an overhead temperature range of 80 to 120° C., a reboiler range of 150 to 200° C., and an operating pressure of 0.1 to 0.7 bar.

18. The method of claim 1, wherein the crude phenol stream is produced by separating an effluent of a cumene based phenol production process.

19. The method of claim 1, wherein the bisphenol-A purge stream includes a bisphenol-A dry mother liquor purge stream generated by crystallization of bisphenol-A from an effluent of a bisphenol-A synthesis reactor.

\* \* \* \* \*